United States Patent [19]

Murata et al.

[11] Patent Number: 4,983,582

[45] Date of Patent: Jan. 8, 1991

[54] PREVENTIVE AND THERAPEUTIC METHOD FOR HYPERTENSION

[75] Inventors: Masakazu Murata, Utsunomiya; Yoshinao Nagashima, Ichikai; Kenji Hara, Utsunomiya; Shigeto Kayane; Takashi Imamura, both of Wakayama, all of Japan

[73] Assignee: Kao Corporation, Tokyo, Japan

[21] Appl. No.: 155,509

[22] Filed: Feb. 12, 1988

[30] Foreign Application Priority Data

Feb. 13, 1987 [JP] Japan .................................. 62-31233

[51] Int. Cl.$^5$ .............................................. A61K 31/70
[52] U.S. Cl. ........................................ 514/23; 514/25; 536/1.1; 536/117
[58] Field of Search ................ 536/1.1, 17.1, 117; 514/23, 25

[56] References Cited

U.S. PATENT DOCUMENTS

| | | | |
|---|---|---|---|
| 3,872,085 | 3/1975 | Penasse et al. | 536/55.3 |
| 3,931,402 | 1/1976 | Ghielmetti et al. | 514/23 |
| 4,006,134 | 2/1977 | Whetstone | 536/117 |

FOREIGN PATENT DOCUMENTS

| | | | |
|---|---|---|---|
| 1468875 | 3/1971 | Fed. Rep. of Germany | 514/23 |
| 2518888 | 11/1976 | Fed. Rep. of Germany | 514/23 |
| 2629845 | 1/1978 | Fed. Rep. of Germany | 514/23 |
| 1351134 | 3/1963 | France | 536/117 |
| 3096M | 2/1965 | France | 536/117 |
| 5145M | 7/1967 | France | 536/117 |
| 43-10620 | 5/1968 | Japan | 536/117 |
| 57-145899 | 9/1982 | Japan | 514/26 |
| 60-130523 | 7/1985 | Japan | 514/23 |
| 0454911 | 4/1975 | U.S.S.R. | 514/23 |
| 1134062 | 11/1968 | United Kingdom | 514/23 |
| 1389763 | 4/1975 | United Kingdom . | |

OTHER PUBLICATIONS

Societe Francaise des Laboratoires Labaz; Chemical Abstracts, 69:27735e (1968).
Roussel-Uclaf; Chemical Abstracts, 70:90746v (1969).
Roussel-Uclaf; Chemical Abstracts, 72:3722 (1970).
Fournier et al; Chemical Abstracts, 74:110204e (1971).
Roussel-Uclaf; Chemical Abstracts, 75:20904z (1971).

*Primary Examiner*—Ronald W. Griffin
*Assistant Examiner*—Nancy S. Carson
*Attorney, Agent, or Firm*—Oblon, Spivak, McClelland, Maier & Neustadt

[57] ABSTRACT

A preventive and therapeutic method for hypertension by dosing hexose phosphate calcium which produces an immediate effect without having any undesirable side-effects to control a rise in the blood pressure, and is efficacious also for various diseases of which onset can be ascribed to hypertension, such as myocardial infarction, cerebral apoplexy, cirrhosis of livers, billiary stasis, and others.

14 Claims, No Drawings

PREVENTIVE AND THERAPEUTIC METHOD FOR HYPERTENSION

BACKGROUND OF THE INVENTION

1. Field of the Invention

The present invention relates to a preventive and therapeutic method for hypertension, and more specifically, to a preventive and therapeutic method for hypertension having an immediate effect and no undesirable side-effects.

2. Description of the Prior Art

Recently with the rapid increase of the death rate due to various adult diseases, it has become an important to develop a preventive and therapeutic method for the diseases of the elderly and aged. Particularly hypertension among them is considered to be a causative factor to adult diseases such as myocardial infarction, cerebral apoplexy, arteriosclerosis, acute hepatitis, cirrhosis, fatty liver, alcoholic hepatitis, billiary stasis; accordingly for prevention and therapy of hypertension, as well as of other diseases which can be ascribed thereto, various kinds of drugs and alimentotherapies have been developed and recommended.

In spite of the extensive studies of hypertension which have been pursued for so many years until today, etiology of hypertension has not yet been elucidated; and the presence of a great variety of antihypertensive drugs of different working mechanisms attests the above stated situation in the medical field.

As drugs which have hitherto been employed to the treatment of hypertension and other diseases resulting therefrom, there may be mentioned; (1) rauwolfia alkaloid, methyl dopa, clonidine and mebutamate which act on the central nervous system, (2) veratrum alkaloid which stimulates chemoreceptors, and causes blood-pressure reduction in the reflex system, (3) methonium compounds, rauwolfia alkaloid, prazosin, propranolol which act on the peripheral sympathetic nervous system, (4) spironolactone acting as a diuretic and hypotensive drug, (5) hydralazine acting on vaso-smooth-muscles, etc.

Those drugs, however, must be administered selectively and properly according to symptoms and conditions of a patient in consideration of the stage of a disease, or they must be administered in combination with other drugs; only one kind of antihypertensive drugs is not sufficient to give an adequate treatment to different symptoms derived from hypertension, not only that, it may occasionally cause serious undesirable side-effects such as palpitation, vertigo, nausea, fever, and others.

Since it is recognized from knowledge of nutrition that an onset of hypertension and intake of sodium are causally related to each other, it is advised that one should be sparing in taking sodium, particularly sodium chloride. That therapy, however, is difficult to practice, because a perfect control of private diets is almost impossible, and because the therapy does not bring an immediate effect on a patient. Under the circumstances, it is hoped that such a preventive and therapeutic method will be developed as soon as possible that will exhibit a sufficient antihypertensive action, and bring an immediate result but having no undesirable side-effects on a patient.

SUMMARY OF THE INVENTION

The present inventors made their assiduous studies to solve the aforesaid problems, and as a result, they found that hexose phosphate calcium has an antihypertensive effect on the patient, and that it is attended with no undesirable side-effects; thus they have brought the findings to the accomplishment of the present invention.

DETAILED DESCRIPTION

The present invention provides a preventive and therapeutic method for hypertension characterized by dosing hexose phosphate calcium.

As hexose phosphate calciums to be used in the present invention may be mentioned phosphate calciums of glucose, fructose, mannose, galactose, tagatose, sorbose, fucose, quinovose, rhamnose, etc., but among them paticularly preferable is phosphate calcium of glucose. Glucose-1-phosphate calcium may be represented, for example, by the following structural formulas (a) and (b), and either one of them may be employed in the present invention;

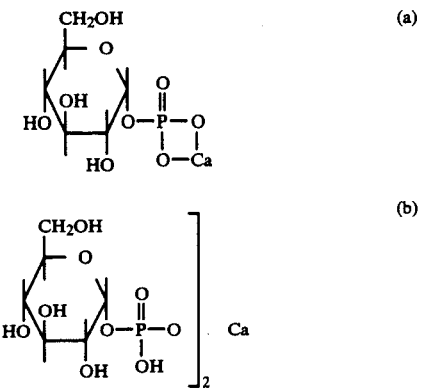

Process for the preparation of glucose-1-phosphate calcium is disclosed in Japanese Patent Publication No. 43-10620, and Japanese Patent Publication No. 56-23998; and physiological effects of the compound, that is, its effect of inhibiting dental caries (Japanese Patent Publication No. 46-7599), cartilage-calcification promotion effect and fatigue-recuperation effect have already been reported, but its antihypertensive effect is unpublished.

In the preventive and therapeutic method for hypertension according to the present invention, hexose phosphate calcium is preferably perorally dosed, and in that case, it is allowed that, if necessary, pharmaceutical carriers or excipients and the like are added thereto to prepare, according to the conventional practice, tablets, granule, and capsules for oral administration. In the preventive and therapeutic method for hypertension, a dose of hexose phosphate calcium is from 0.1 to 20 g/day, preferably from 1 to 15 g/day, for an adult.

Incidentally, glucose-1-phosphate calcium is a very safe drug, because only when it is dosed perorally to a mouse in an amount of 15,000 mg/kg body weight or more, it exhibits an acute toxicity.

The preventive and therapeutic method for hypertension according to the present invention has enabled not only to hinder an increase in the blood pressure, but also to prevent and treat, without appearance of any undesirable side-effects, many diseases such as myocardial infarction, cerebral apoplexy, liver cirrhosis, billiary stasis, etc., whose onset can be ascribed to hypertension.

EXAMPLES

The present invention will be more clearly understood by reference to the following examples; however, the examples are intended to illustrate the invention and are not to be construed to limit the scope of the invention.

Example 1: Blood pressure comparison

To each group comprising 10 male SHR of approx. 300 g of the body weight was per orally dosed 3 ml/day of the following aqueous solutions for 3 months;

an aqueous solution of glucose-1-phosphate calcium (2 g/100 ml) represented by the structural formula (a), and an aqueous solution of glucose-1-phosphate calcium containing compounds of the general formulas (a) and (b) in the weight ratio of 9:1, while to a control group was given distilled water.

The systolic blood pressure was measured at the tail of each subject, every one, two and three months of the administration period.

The test result is shown on Table 1.

TABLE 1

| Systolic blood pressure of SHR-rat at tail | | | |
|---|---|---|---|
| | 1 month | 2 months | 3 months |
| Control Group (n = 10) | 150 | 187 | 215 |
| Glucose-1-phosphate calcium (a) (n = 10) | 148 | 153 | 155 |
| Glucose-1-phosphate calcium of (a) and (b) mixed in a ratio of (a)/(b) = 9:1, (n = 10) | 150 | 165 | 158 |

(Values on the table signify average values.)

The test result on Table 1 proves that rise in the blood pressure was effectively controlled by the preventive and therapeutic method for hypertension according to the present invention, as compared with the control group.

Example 2: Blood pressure comparison

To each group comprising 10 male SHR at the age of 9 weeks was dosed average 30 ml/day of the following aqueous solutions for 15 weeks;

an aqueous solution of glucose-1-phosphate calcium (1 g/100 ml) represented by the structural formula (a), an aqueous solution of calcium lactate (0.83 g/100 ml), and an aqueous solution of hydrochlorothiazide (0.093 g/100 ml), which is one of the thiazide diuretics, while to a control group was dosed distilled water.

Systolic blood pressure was measured in a closed method in the tail artery of the subject at each time of before administration, 5 weeks of administration, and 15 weeks of administration (the measuring apparatus employed was PS-200 of Rikenkaihatsu Co.).

Results of the measurements are shown on Table 2.

TABLE 2

| Systolic blood pressure in the SHR | | | |
|---|---|---|---|
| | before administration | 5 weeks after | 15 weeks after |
| Control Group (n = 10) | 197 | 203 | 211 |
| Glucose-1-phosphate calcium (a) (n = 10) | 199 | 175 | 185 |
| Calcium lactate (n = 10) | 198 | 190 | 204 |
| Hydrochlorothiazide (n = 10) | 200 | 175 | 188 |

(Values on the table signify average)

From the above test result it is clear that the administration of glucose-1-phosphate calcium reduces the systolic blood pressure of SHR-rat substantially in the same extent as hydrochlorothiazide which is one of the thiazide diuretics.

We claim:

1. A method of inhibiting hypertension in a mammal, which comprises administering to said mammal an effective amount of a calcium salt of a hexose phosphate.

2. The method according to claim 1, wherein said calcium salt of a hexose phosphate is perorally dosed.

3. The method according to claim 1, wherein said mammal is an adult human.

4. The method according to claim 3, wherein said effective amount of said calcium salt of a hexose phosphate is from 0.1 to 20 g/day.

5. A method of treating hypertension in a mammal, which comprises administering to said mammal an effective amount of a calcium salt of a hexose phosphate.

6. The method according to claim 5, wherein said calcium salt of a hexose phosphate is perorally dosed.

7. The method according to claim 5, wherein said mammal is an adult human.

8. The method according to claim 6, wherein said effective amount of said calcium salt of a hexose phosphate is from 0.1 to 20 g/day.

9. The method according to claim 1, wherein said hexose phosphate is selected from the group consisting of glucose, fructose, mannose, galactose, tagatose, sorbose, fucose, quinovose and rhamnose.

10. The method according to claim 9, wherein said hexose phosphate is glucose.

11. The method according to claim 4, wherein said effective amount is from 1 to 15 g/day.

12. The method according to claim 5, wherein said hexose phosphate is selected from the group consisting of glucose, fructose, mannose, galactose, tagatose, sorbose, fucose, quinovose and rhamnose.

13. The method according to claim 12, wherein said hexose phosphate is glucose.

14. The method according to claim 8, wherein said effective amount is from 1 to 15 g/day.

* * * * *